United States Patent
Gentry et al.

(10) Patent No.: US 7,202,486 B2
(45) Date of Patent: Apr. 10, 2007

(54) TREATMENT PLANNING TOOL FOR MULTI-ENERGY ELECTRON BEAM RADIOTHERAPY

(75) Inventors: John R. Gentry, Freeport, IL (US); Christopher J. Kubiak, Middleton, WI (US); Keith R. Nelson, Waunakee, WI (US); Bhudatt R. Paliwal, Madison, WI (US); Raymond T. Riddle, Middleton, WI (US); Myles L. Sommerfeldt, Madison, WI (US); Richard A. Steeves, Madison, WI (US)

(73) Assignee: Standard Imaging, Inc., Middleton, WI (US)

(*) Notice: Subject to any disclaimer, the term of this patent is extended or adjusted under 35 U.S.C. 154(b) by 234 days.

(21) Appl. No.: 10/910,837

(22) Filed: Aug. 4, 2004

(65) Prior Publication Data

US 2006/0033044 A1 Feb. 16, 2006

(51) Int. Cl.
*A61N 5/00* (2006.01)
*G21G 5/00* (2006.01)

(52) U.S. Cl. .............................. 250/492.1; 250/492.1; 250/492.3

(58) Field of Classification Search .............. 250/492.1, 250/492.3
See application file for complete search history.

(56) References Cited

U.S. PATENT DOCUMENTS 5,440,133 A * 8/1995 Moyers et al. ........... 250/492.3
6,459,762 B1 * 10/2002 Wong et al. ................. 378/65

OTHER PUBLICATIONS

Kenneth R. Hogstrom, et al., Modulated Electron Therapy; Medical Physics Monograph No. 29, Intensity-Modulated Radiation Therapy, The State of the Art; Jun. 22-26, 2003, pp. 749, 762-763; Medical Physics Publishing, Madison, Wisconsin.

* cited by examiner

*Primary Examiner*—Jack Berman
*Assistant Examiner*—Jennifer Yantorno
(74) *Attorney, Agent, or Firm*—Boyle Fredrickson Newholm Stein & Gratz S.C.

(57) ABSTRACT

A stand-alone calculator enables multi energy electron beam treatments with standard single beam electron beam radiotherapy equipment thereby providing improved dose profiles. By employing user defined depth-dose profiles, the calculator may work with a wide variety of existing standard electron beam radiotherapy systems.

22 Claims, 2 Drawing Sheets

TREATMENT PLANNING TOOL FOR MULTI-ENERGY ELECTRON BEAM RADIOTHERAPY

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates to electron beam radiation therapy (radiotherapy) treatment of tumors and the like and in particular to a treatment planning tool providing improved dose profile for electron beam radiation therapy machines.

Radiotherapy treats tissue with high-energy radiation. The amount of radiation and its placement must be accurately controlled to ensure both that the tumor receives sufficient radiation to be destroyed and that the damage to the surrounding and adjacent non-tumorous tissue is minimized.

External source radiotherapy may use high-energy radiation such as photons or electrons. In electron beam radiotherapy, a source of electrons, for example from a linear accelerator, may be directed toward the patient at a given angle and collimated to a given beam size (cone size). The energy of the electrons may be set, typically to one or more discrete energy levels of 4, 6, 9, 12, 15, 16, 18, 20 or 22 MeV. Typical cone sizes include 4×4, 6×6, 10×10, 15×15, 20×20, and 25×25 cm. The cumulative flux and hence the dose may be controlled by controlling the monitor units ("MU") of the radiation therapy machine through direct control of the linear accelerator current and/or control of the exposure time.

Electrons have a particular advantage in the treatment of some superficial cancers such as skin, breast, head and neck tumors, and intraoperative surgical procedures in that they provide rapid falloff as a function of penetration depth. Control of the depth of falloff of the electron beam may be provided by use of a customized bolus, being typically a water equivalent or tissue mimicking material placed on the patient's skin to provide some initial interaction with the electrons before the electrons reach the region targeted for treatment.

Standard electron beam radiation therapy machines are essentially "single-beam" devices providing a single, essentially constant and uniform electron beam. More sophisticated "intensity modulated" radiation treatment machines and treatment planning systems have been proposed in which the electron beam is divided into "beamlets", each separately modulated by intensity and/or energy. A complex inverse treatment planning technique, for example, a Monte Carlo based algorithm, would be used to optimize the fluence and energy of the many beamlets over multiple treatments. Such equipment and the necessary planning tools are not available in most clinical settings.

BRIEF SUMMARY OF THE INVENTION

The present invention provides a treatment planning tool that allows the benefits of treatments using the multiple electron beam energies or combined electron/photon energies available on a standard, single beam radiotherapy system. The tool, which may operate on a stand-alone desktop computer, accepts a simple characterization of a desired beam depth dose profile and produces a multiple energy treatment plan that can be entered into a radiation therapy treatment planning system and implemented using successive exposures from the radiation therapy machine.

Specifically, the present invention provides a treatment planning tool for use with a standard electron beam radiation therapy machine of a type which produces a spatially unmodulated electron beam at one of a predetermined set of electron energies. The treatment tool comprises a program executing on a computer to accept a dose description indicating a desired dose as a function of depth along a central axis of the beam, and to determine from that desired dose description, a set of sequential electron energy exposures using a different electron energy and/or bolus that satisfies the dose description. Photon beams may optionally be combined with electron beams. The tool then outputs the expected depth dose distribution exposure data and the method by which the depth dose distribution may be achieved for input into a radiation therapy treatment planning system for the ultimate setting of the electron beam radiation therapy machine.

Thus it is one object of at least one embodiment of the invention to improve the depth-dose profiles obtainable on standard radiation therapy machines by assisting a radiation therapy treatment planning system in combining multiple electron beam energies.

The program may output a graph showing a plot of a dose of the combined sequential electron energy exposures as a function of depth.

It is thus another object of at least one embodiment of the invention to provide a simple and intuitive display of the results of the electron treatment plan that may be used to verify the suitability of the treatment plan or to allow one treatment plan of multiple different treatment plans to be selected by the user.

The graph may also show a plot of dose as a function of depth for each electron energy alone.

It is thus another object of at least one embodiment of the invention to provide a simple method of visually confirming the results of the electron treatment plan.

The tool may determine multiple combinations of sequential electron energy exposures with different energies and the program may output graphs having plots showing a dose as a function of depth for each combination. The user may select from these combinations or the tool may select along the combinations at least one best satisfying the dose description.

Thus it is an object of at least one embodiment of the invention to provide a comprehensive view of a variety of electron combination treatment options obtainable on a particular electron beam radiation therapy machine.

The dose description may comprise a first skin dose value and a second tissue dose value at a predetermined location beneath the skin.

It is thus another object of at least one embodiment of the invention to provide a simple description of the desired dose such as may be manually entered into a stand-alone computer running the present program.

The dose description may include a homogeneity limit defining a maximum variation in specified dose over a depth range and/or a range defining a maximum dose at a range location.

Thus it is another object of at least one embodiment of the invention to provide a simple method of characterizing a depth-dose curve as may be manually entered into a stand alone computer running the present program.

The program may accept multiple files providing percent depth dose profiles for different electron or photon energies for a specific electron beam radiation therapy machine.

These files may be used in determining the dose produced by the combined sequential electron or electron/photon energy exposures.

Thus it is an object of at least one embodiment of the invention to provide a tool that may be used with a wide variety of standard electron beam radiation therapy machines as characterized by the files without the need for complex mathematical modeling or the like.

A different file may be provided for each different cone size for the standard electron beam radiation therapy machine.

Thus it is another object of at least one embodiment of the invention to capture changes in depth-dose profiles caused by changes in cone sizes.

The exposures of the combined exposure may each employ a different bolus thickness.

Thus it is another object of at least one embodiment of the invention to provide the ability to tailor both energy and bolus thickness to optimize the depth dose profiles.

These particular objects and advantages may apply to only some embodiments falling within the claims and thus do not define the scope of the invention.

DETAILED DESCRIPTION OF THE PREFERRED EMBODIMENT

Figure 1:
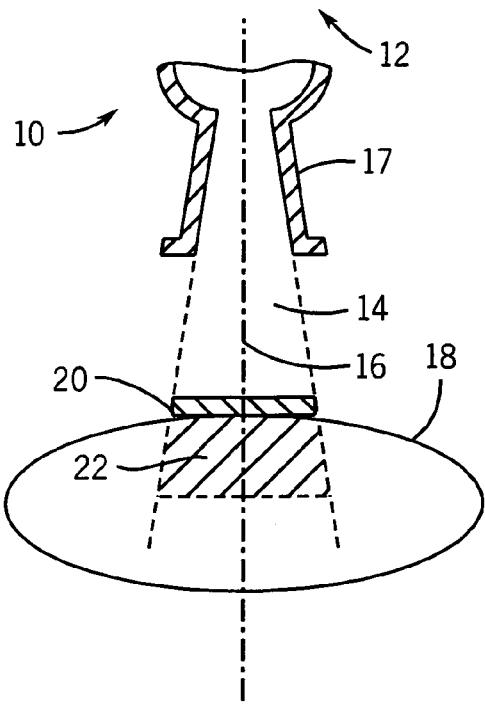
FIG. 1 is a simplified cross-sectional representation of an electron beam radiation therapy machine treating a patient having a skin placed bolus.

Referring now to FIG. 1, a standard electron beam radiation therapy machine 10 may include a linear accelerator 12 (not shown) producing an electron beam 14 centered along central beam axis 16 as collimated by cone 17 and directed toward a patient 18. The electron beam 14 may pass through a bolus 20 placed on the patient's skin and then pass into a treatment region 22 of the patient. A target (not shown) can be placed in the electron beam 14 to allow for the production of x-ray photons.

Figure 2:
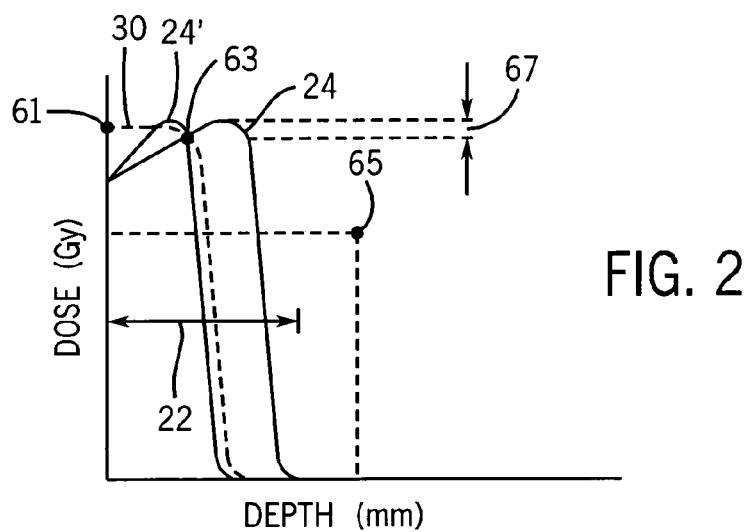
FIG. 2 is a percent depth dose profile of two energies of the electron beams and the resultant combined percent depth dose profile produced by the present invention.

Referring now to FIG. 2, the electron beam 14 deposits a dose in the treatment region 22 described by a depth-dose profile 24 providing dose as a function of depth defined with respect to the patient's skin surface. Typically, the depth-dose profile 24 rises slightly to a peak and then falls off abruptly. The exact shape of the depth-dose profile 24 will vary (e.g. depth-dose profile 24') based on the energy of the electron beam 14, the size of the cone 17 and the model of linear accelerator 12.

The height of the depth-dose profile 24 and 24' (thus the absolute dose) may be changed by controlling the monitor units (MU) of the exposure. The energy of the electron beam 14 and the MU of the exposure are controlled by settings on the radiation therapy machine 10 as is well understood in the art.

The standard electron beam radiation therapy machine 10 is characterized by the fact that the electron beam 14 is relatively constant in profile, unmodulated over its area by multi-leaf collimators or the like.

In the present invention, two or more electron beams 14 having different energies are used sequentially to produce two or more depth-dose profiles 24 and 24' which combine to produce a composite depth-dose profile 30 with superior characteristics, for example, better homogeneity inside the treatment region 22 and/or improved fall off outside of the treatment region. Generally the composite depth-dose profile 30 will be a point-by-point summing of the values of two sequential depth-dose profiles 24 and 24'.

Figure 3:
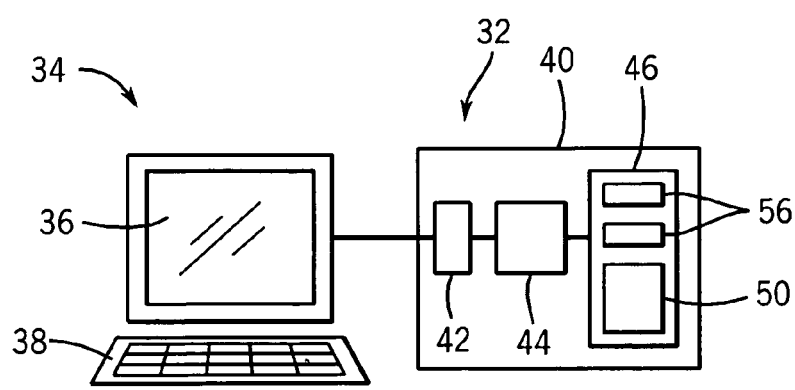
FIG. 3 is a block diagram of a standard desktop computer system suitable for implementing the present invention as a program.

Referring now to FIG. 3, the present invention provides a tool to generate settings for a standard electron beam radiation therapy machine 10 that will produce a composite depth-dose profile 30. In the preferred embodiment, the tool uses a standard desktop computer system 32 having a graphic display terminal 34 including a display screen 36 and a data entry device 38 such as a keyboard and trackball or mouse. The terminal 34 may communicate with a processor unit 40, the latter having an interface circuit 42 of a type well known in the art. The interface circuit 42 in turn, communicates with a processor 44 and memory 46, the latter holding data files 56 and a program 50 reading the data files 56 and executing the method of the present invention. As will be understood in the art, the computer system 32 need not and, in the preferred embodiment, does not have direct electrical connection to the radiation therapy machine 10 of FIG. 1, but rather receives data solely through the data entry device 38 from a human user and displays data on the display screen 36 or through a printer (not shown) to a human user for manual setting of the standard electron beam radiation therapy machine 10.

Figure 4:
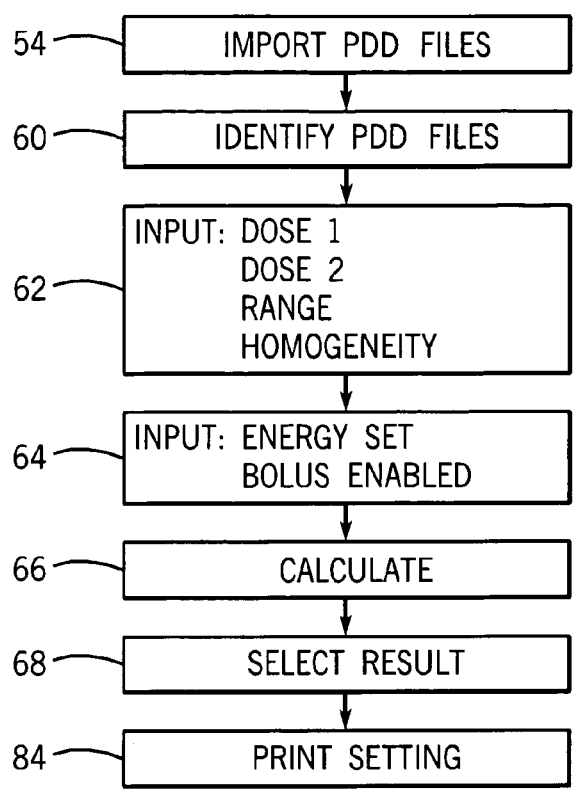
FIG. 4 is a flow chart showing the steps of the execution of the program of FIG. 4 and implementing the present invention.

Referring now to FIG. 4, the method of the present invention starts with the collection of data for the data files 56. These data files 56 hold percent depth dose data (PDD) taken along the central axis 16 of the standard electron beam radiation therapy machine 10. The PDD data is essentially a depth-dose profile 24 normalized to a standard MU value and is collected for each energy of electron beam 14, each cone size, and each linear accelerator 12. In an alternative embodiment, the PDD data for different cone sizes may be measured for each cone 17 and applied to collected PDD data for each energy. The PDD data can be obtained by measurements of the particular linear accelerator 12 using standard phantoms and calibration techniques well known in the art, and once obtained, may be imported by the program in memory 46 as shown in process block 54.

The PDD data provides dose values every millimeter and may be formatted and accepted by the program 50 in standard spread sheet formats for operator convenience.

During the importation process of process block 54, each file of PDD data is identified by cone size, beam energy, and a description of the particular linear accelerator by model number, serial number, and location so that this information can be read by the program 50 as well as the PPD data. This identification process is indicated by process block 60. The entry identifying information about the PDD data may be facilitated by a graphical menu appearing on the display screen 36 and generated by the program 50 and prompting the user as necessary.

After the collection of the PDD data, an electron treatment plan may be initiated. As indicated by process block 62 at the beginning of the treatment process, the user is prompted to enter descriptions of a desired depth dose profile. Referring again also to FIG. 2, this description does not require a full set of data points per the PDD but in the preferred embodiment is captured by a first dose value 61 at the skin and a second dose value 63 at a designated depth below the skin.

At this time, the user also enters a range value 65 (in the form of a percent of first dose value 63) at a predetermined depth outside the treatment region 22. The range value will be used to test for a desired fall off in the dose in the composite depth-dose profile 30 to be produced. Finally the user will enter a homogeneity value 67 being a percent deviation in dose between the skin and the location of second dose value 63 for the composite depth-dose profile 30.

Once this data is entered, and as indicated by process block 64, the user may set two desired beam energies that will be considered in the treatment plan typically from a set of fixed energies provided by the standard electron beam radiation therapy machine 10. The user may also enable the use of the boluses in developing a treatment plan by checking an appropriate menu check box on the display screen 36.

Once this data is collected, a treatment plan within these constraints is determined as indicated by process block 66.

Generally, the dose D(x) at any depth x in standard tissue of a patient at an electron beam energy $E_n$ will be equal to:

$$D_n(x) = MU_n PDD_n(x)$$

where $MU_n$ is monitor units of the electron beam 14, $PDD_n$ is percent depth dose along the central axis 16 of a specific electron energy, measured as described above. All calculations are done on the central axis 16 substantially simplifying the problem and the evaluation of the solutions.

Accordingly the dose at a series of depth location points $x_1, x_2, \ldots, x_m$ defining a composite depth-dose profile 30 for the two or more selected beam energies will be defined by a series of equations as follows:

$$D(x_0) = MU_1 PDD_1(x_0) + MU_2 PDD_2(x_0) \ldots MU_n PDD_n(x_0)$$
$$D(x_1) = MU_1 PDD_1(x_1) + MU_2 PDD_2(x_1) \ldots MU_n PDD_n(x_1)$$
$$\vdots$$
$$D(x_m) = MU_1 PDD_1(x_m) + MU_2 PDD_2(x_m) \ldots MU_n PDD_n(x_m)$$

As will be understood to one of ordinary skill in the art, these equations may be generalized for treatment at more than one energy in an alternative embodiment of the invention.

Dose values 61 and 63 are substituted into the appropriate D(x) values and these equations are solved by standard matrix algebra techniques to yield a set of solutions providing MU values for the two or more electron beams 14. This set of solutions is tested against the range and homogeneity values previously input.

If the use of boluses has been enabled as described above, this calculation is repeated for each of a set of different bolus thicknesses by modifying the above equations as follows:

$$D(x_0) = MU_1 PDD_1(x_0 + \delta) + MU_2 PDD_2(x_0 + \delta) \ldots MU_n PDD_n(x_0 + \delta)$$
$$D(x_1) = MU_1 PDD_1(x_1 + \delta) + MU_2 PDD_2(x_1 + \delta) \ldots MU_n PDD_n(x_1 + \delta)$$
$$\vdots$$
$$D(x_m) = MU_1 PDD_1(x_m + \delta) + MU_2 PDD_2(x_m + \delta) \ldots MU_n PDD_n(x_m + \delta)$$

where δ is an effective offset in depth created by the bolus thickness. For simplicity, only bolus thicknesses differing by at least one millimeter, are considered and a predetermined range of bolus thickness ranges are determined (by a look up table) integrated into the program 50 tailored to each energy level as will be understood to those of ordinary skill in the art. Generally lower electron beam energies will have smaller maximum bolus sizes. Thus, for example, at 4 MeV a maximum bolus of 16 millimeters may be provided in this table, whereas at 22 MeV a maximum bolus size of 105 millimeters will be considered.

The solutions obtained using boluses are added to the solution set to be tested against the requirements of range and homogeneity. Generally, when a bolus is used, a solution may include two different beam energies that pass through different thicknesses of boluses, or a solution may include two beam energies that are the same but that pass though different thicknesses of boluses, or a bolus may be used with only one beam and the second beam may have no bolus, or two different energies may be used with boluses of the same thickness.

In the event that there is no solution, the user is informed of such and prompted to consider relaxing the homogeneity and/or range requirements.

Figure 5:
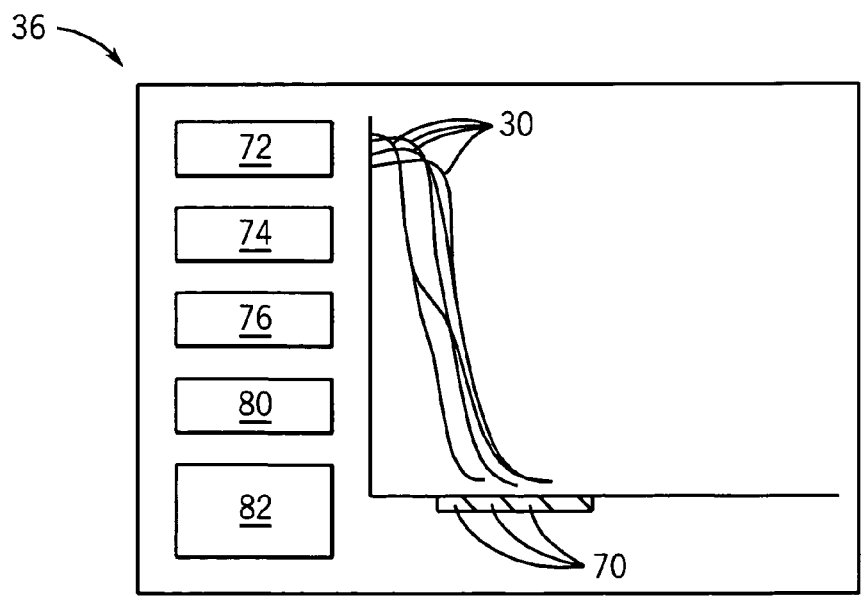
FIG. 5 is a simplified display produced on the computer system of FIG. 3 as facilitates the entering and outputting of treatment data.

More typically referring to FIG. 5, when multiple solutions are obtained, the program may select one solution according to predetermined criteria or, in the preferred embodiment, a predetermined number of these solutions may be presented on the display screen 36 by plots of the composite depth-dose profiles 30 corresponding to the solutions. Each composite depth-dose profile 30 is of a different color and associated with a tab 70 of corresponding color. When a given tab 70 is pressed, the graphic display presents detailed data associated with that solution.

Referring to FIGS. 2 and 5, the data available upon pressing a tab 70 will include a depiction of normalized PDD depth-dose profile 24 and 24' associated with the user selected beam energies and a depiction of the composite depth-dose profile 30 associated with that tab 70. The user may quickly verify the plausibility of the solution and may see the extent to which it improves upon either of the two beam energies used individually. Note that generally the composite depth-dose profile 30 will be in absolute dose values whereas the depth-dose profile 24 and 24' will be in percent dose values.

Pressing a tab 70 also provides detailed numeric information about the selected choice including relative monitor units needed for each exposure with the different beams in text box 72. These monitor units may be as an input to a radiation therapy treatment planning system prior to being used to manually set the standard electron beam radiation therapy machine 10 to implement the composite depth-dose profile 30.

The display screen 36 also provides numeric readings at text box 76 giving the total dose contribution provided at each electron beam 14 at each energy level, tabular numeric values of the composite depth-dose profile 30 indicated by text box 80 and a summary 82 of the values that will then be put into a radiation therapy treatment planning system, providing a description of the cone size, the particular energies selected and the other information entered at process block 60 and 62.

Referring now to FIG. 4, once the desired composite depth-dose profile 30 is selected as indicated by process block 84, the screen and output data may be printed to provide a permanent record of the electron solutions treatment plan.

Typically, the output data will be input to treatment planning software that may model a dose in three dimensions using the beam energies selected. Such software may be part of a treatment planning system, for example, that is normally used for inverse treatment planning. After the modeled dose is checked and possibly refined, the output data is used to control the radiation therapy machine.

As will be understood from the above description, the invention may be readily extended to combinations of electron beams and one or more photon beams simply by preparing the necessary PDD files for the photon beams and allowing the program to consider combinations of electron and photon beams with different depth dose profiles. Photon beams will not typically use boluses.

It is specifically intended that the present invention not be limited to the embodiments and illustrations contained herein, but include modified forms of those embodiments including portions of the embodiments and combinations of elements of different embodiments as come within the scope of the following claims.

We claim:

1. A treatment planning tool for use with a standard electron beam radiation therapy machine producing a spatially unmodulated electron beam at one of a predetermined set of electron energies, the treatment planning tool comprising a program embodied in a computer readable medium, the program executing on a computer to:
   (a) accept a dose description that is unrealizable with electrons of a single energy passing through a given bolus, the dose description indicating a desired dose as a function of depth along a central axis of the electron beam;
   (b) determine a combination of sequential electron energy exposures using the electron beam radiation therapy machine, each exposure employing an electron beam with a different depth-dose profile so that the combination of sequential electron energy exposures satisfies the dose description; and
   (c) output data for implementing each sequential exposure on the electron beam radiation therapy machine.

2. The treatment planning tool of claim 1 wherein the sequential electron energy exposures employ different electron beam energies.

3. The treatment planning tool of claim 1 wherein the sequential electron energy exposures employ different bolus amounts.

4. The treatment planning tool of claim 1 wherein the program further outputs a graph showing a plot of a depth-dose profile of a combined sequential electron energy exposure.

5. The treatment planning tool of claim 4 wherein the graph also shows a plot of a depth-dose profile of each constituent sequential electron energy exposures alone.

6. The treatment planning tool of claim 1 wherein the program determines multiple combinations of sequential electron energy exposures with different depth-dose profiles and wherein the program further outputs graphs having plots showing a depth-dose profile of each combination.

7. The treatment planning tool of claim 6 wherein the program further accepts input from a user to select one of the combinations and the output data is for that selected one of the multiple combinations.

8. The treatment planning tool of claim 1 wherein the program determines multiple combinations of sequential electron energy exposures with different energies and selects among the combinations at least one best satisfying the dose description.

9. The treatment planning tool of claim 1 wherein the dose description comprises a first dose value and a second dose value, each at a different predetermined location.

10. The treatment planning tool of claim 1 wherein the dose description comprises a homogeneity limit defining a maximum variation in dose over a depth range.

11. The treatment planning tool of claim 1 wherein the description includes a range defining a maximum dose at a location.

12. The treatment planning tool of claim 1 wherein the program further accepts multiple files providing percent depth-dose for different electron energies for a specific electron beam radiation therapy machine and wherein the determining of exposures uses data of the files to determine a depth-dose profile produced by a combined sequential electron energy exposure.

13. The treatment planning tool of claim 12 wherein the program further accepts multiple files providing percent depth-dose for different cone sizes for a specific electron beam radiation therapy machine and wherein the step of determining uses data of the files to determine a dose produced by the combined sequential electron energy exposures.

14. The treatment planning tool of claim 1 wherein a user further inputs desired electron beam energies and the program constrains its determination of a combination of sequential electron energy exposures using the electron beam radiation therapy machine to input the electron beam energies.

15. The treatment planning tool of claim 1 further including a treatment planning program wherein the treatment planning program models a dose produced over three dimensions using the output data before use of the output data on the electron beam radiation therapy machine.

16. A treatment planning tool for use with a standard radiation therapy machine producing a spatially unmodulated electron beam and a spatially unmodulated photon beam at predetermined energies, the treatment planning tool comprising a program embodied in a computer readable medium, the program executing on a computer to:
   (a) accept a dose description that is unrealizable with electrons or photons of a single energy, the dose description indicating a desired dose as a function of depth along a central axis of the electron beam;
   (b) determine a combination of sequential exposures including at least one electron beam and one photon beam, each exposure providing a different depth-dose profile so that the combination of sequential exposures satisfies the dose description; and
   (c) output data for implementing each sequential exposure on the radiation therapy machine.

17. A treatment planning tool for use with an electron beam radiation therapy machine producing an electron beam at one of a predetermined set of electron energies, the treatment planning tool comprising a program embodied in a computer readable medium, the program executing on a computer to:
   (a) accept a dose description that is unrealizable with electrons of a single energy passing through a single bolus, the dose description indicating a desired dose as a function of depth for use with a radiation therapy treatment planning system to produce a treatment plan;

(b) determine a combination of sequential electron energy exposures using the electron beam radiation therapy machine, each exposure employing an electron beam with a different electron energy so that the combination of sequential electron energy exposures satisfies the dose description; and (c) output a graphical plot showing dose as a function of depth for the combination of sequential electron energy exposures.

18. The treatment planning tool of claim 17 wherein the graph also shows a plot of a dose as a function of depth of each constituent sequential electron energy exposure alone.

19. The treatment planning tool of claim 17 wherein the program determines multiple combinations of sequential electron energy exposures with different energies and wherein the program further outputs graphs having plots showing a dose as a function of depth of each combination.

20. The treatment planning tool of claim 19 wherein the program further accepts input from a user to select one of the combinations and the output graphical plot is for that selected one of the multiple combinations.

21. The treatment planning tool of claim 17 wherein at least one exposure employs a bolus.

22. A method of electron beam radiotherapy comprising the steps of:

(a) preparing a dose description that is unrealizable with electrons of a single energy passing through a given bolus, the dose description indicating a desired dose as a function of depth along a central axis of the electron beam;

(b) executing a program on a computer to accept the dose description for use with a radiation therapy treatment planning system to prepare a treatment plan for a standard electron beam radiation therapy machine using at least two spatially unmodulated electron beams at different energies so that a combination of sequential electron energy exposures satisfy the dose description; and (c) manually setting the standard electron beam radiation therapy machine to expose a treatment area of a patient at a first time with a first electron beam at a first energy and at a second time with a second electron beam at a second energy according to the treatment plan.

* * * * *